United States Patent [19]
Durand et al.

[11] Patent Number: 5,174,966
[45] Date of Patent: Dec. 29, 1992

[54] LABORATORY DEVICE AND METHOD FOR TREATING ROCK SAMPLES

[75] Inventors: Bernard Durand, Rueil Malmaison; Thierry Lesage, Tessancourt Sur Aubette; Jean-Claude Monin, Cormeilles En Parisis; Jean-Max Charpentier, Rueil Malmaison, all of France

[73] Assignee: Institut Francis du Petrole, Rueil Malmaison, France

[21] Appl. No.: 567,181

[22] Filed: Aug. 14, 1990

[30] Foreign Application Priority Data

Aug. 14, 1989 [FR] France ................... 89 10957

[51] Int. Cl.⁵ .................... B01D 11/02; G01N 33/24
[52] U.S. Cl. .................... 422/102; 422/227; 422/231; 422/261; 436/25; 436/29; 436/31; 196/14.52; 210/406; 210/407; 210/511; 210/633; 210/634
[58] Field of Search ............... 422/101, 102, 227, 231, 422/261, 267; 436/25, 29, 31; 196/14.52; 210/406, 407, 511, 633, 634

[56] References Cited

U.S. PATENT DOCUMENTS

| | | | |
|---|---|---|---|
| 1,060,010 | 4/1913 | Murray et al. | 196/14.52 |
| 1,123,542 | 1/1915 | Janensch | 422/261 X |
| 4,153,415 | 5/1979 | Espitalie et al. | 436/31 |
| 4,387,110 | 6/1983 | Emmi et al. | 422/261 X |
| 4,610,847 | 9/1986 | Hood et al. | 422/102 |
| 5,032,515 | 7/1991 | Tanigaki et al. | 422/231 X |

*Primary Examiner*—Robert J. Warden
*Assistant Examiner*—Stephanie Blythe
*Attorney, Agent, or Firm*—Antonelli, Terry, Stout & Kraus

[57] ABSTRACT

A laboratory device and method are adapted to subject a same rock sample to successive liquid treatments without any intermediary handling of the sample. The device combines a chamber comprising a first part fitted with an inlet for introducing a rock sample and liquid reagents into the chamber; a heater for regulating the temperature in the chamber and a plug fitted within an open port for protecting the chamber from an overpressure. The first part also comprises means for stirring the contents of the chamber including a liquid by introducing gas as bubbles into the liquid. A second part of the chamber is located under the first part and a selective filtering unit is interposed between the first and second parts of the chamber, the filter has a porosity selected for retaining organic material contained in the sample. A gas bubbling inlet is provided for introducing the gas into the liquid contained in the chamber and a valve controlled discharge opening is also provided for draining off liquid from the chamber.

10 Claims, 1 Drawing Sheet

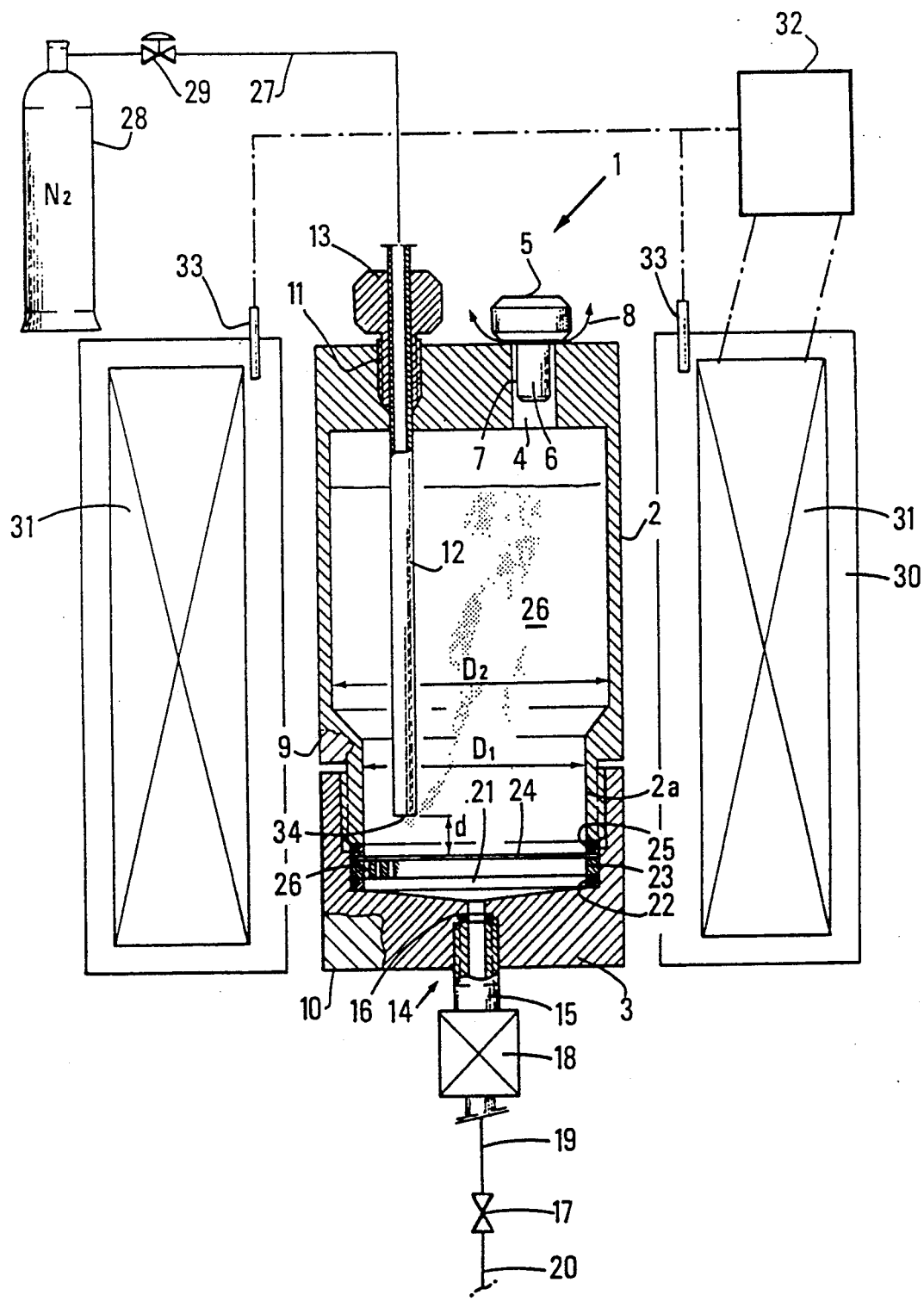

LABORATORY DEVICE AND METHOD FOR TREATING ROCK SAMPLES

BACKGROUND OF THE INVENTION

The object of the present invention is an improved laboratory device and a method for subjecting the same rock sample to successive treatments, without any intermediary handling. The device according to the present invention particularly improves the laboratory techniques for isolating the organic matter fraction which is contained in the rocks and which cannot be extracted by solubilization.

These isolation techniques generally comprise the use of mineral acids for solubilizing the constituent minerals of the rock, after grinding the rock. Hydrochloric acid is first utilized for solubilizing the carbonates, then hydrofluoric acid is used for solubilizing the silicates. Additional treatments are sometimes carried out to solubilize some of the minerals standing up to the previous treatments. It can for example be attempted to solubilize the pyrite, or a fraction of it, by means of hydrogenating or oxidizing reagents.

At the end of these treatments, the insoluble organic matter is recovered by centrifuging or by filtering. Centrifugings or filterings are also necessary between these different treatments. The total treatment time is very long and may reach several hundred hours, notably if one wishes to isolate from certain rocks an organic matter no longer containing more than an amount of mineral impurities sufficiently low for the subsequent analyses to be carried out in good conditions. Besides, the quality of the preparations is often poorly reproducible, the handlings are numerous and are performed in non-satisfactory security conditions.

Prior art can be illustrated by French Patent 2,290,666.

The devices according to prior art utilize mechanical stirring means for stirring the mixture of reagent and rock.

These means have serious drawbacks. On one hand, the stirring element, which is often a helix, wears out and is affected by the aggressive products that are used for treating the rock sample. The products of this parasitic attack may distort the measurements. On the other hand, such a stirring device requires the use of a shaft, a helix, an electric engine, pulleys, belts and/or speed reducers. The use of such parts makes the equipment bulky and uneasy to handle.

Besides, these parts are easily damaged by heat while the treating of the rock sample generally requires at least one operation involving an increase in temperature.

SUMMARY OF THE INVENTION

Thus, in a general way, the laboratory device according to the present invention subjects the same rock sample to successive treatments without any intermediary handling. This device combines a chamber comprising a first part fitted with means for introducing the sample and the reagents, means for regulating the temperature in the chamber and means for protecting this chamber from an inner overpressure, said first part of the chamber also comprising means for stirring a liquid, a second part of the chamber located under said first part, selective filtering means interposed between said first and second parts of the chamber and having a porosity selected for retaining the organic matter contained in the sample, means tightly joining said first part of the chamber, said filtering means and said second part of the chamber, means for draining off the liquids passing across said filtering means and gathering in said second part of the chamber and means for controlling at will the stopping of this draining off. The device according to the invention is characterized in that said stirring means comprise a bubbling gas inlet adapted for achieving the stirring of the liquid contained in said chamber and means for liberating the bubbling gas from the chamber.

The bubbling gas inlet can be connected to a nitrogen source.

The d/D ratio can range from 0.15 to 0.25 and preferably from 0.17 to 0.21, d being the distance between the filtering means (24) and the location in the chamber which said gas inlet opens into, and D is the average hydraulic diameter of the chamber.

The device according to the invention can comprise means for controlling the flow of bubbling gas. These means are adapted for delivering a gas flow ranging from 0.2 to 0.3 times the volume of the liquid contained in the chamber per minute.

The temperature regulation means can comprise an electronically controlled metallic heating unit.

The means for liberating the bubbling gas can comprise a plug which is kept in position in an entrance part by gravity on a substantially horizontal surface borne by said first part.

BRIEF DESCRIPTION OF THE DRAWING

The present invention and its advantages will be clear from reading the description hereafter of a particular, non limitative example with reference to the accompanying drawing showing a preferred embodiment of the device.

DESCRIPTION OF THE PREFERRED EMBODIMENT

The device according to the invention as shown in the drawing comprises a cell 1 consisting of two parts an upper body 2 and a lower body 3.

The upper body comprises, in the neighborhood of its upper end, a port 4 used for filling the cell and adapted to receive a plug 5. This plug is set on the upper end and is advantageously held there, i.e. the forces of gravity keep it in position. The extended part 6 of plug 5 and the bore of port 4 which cooperate with it show a clearance 7 that is sufficient for allowing gas circulation and liberation of the gas as shown by arrows 8. This liberation of course takes place through the lifting of plug 5 as a result of a slight overpressure in the cell, this overpressure being controlled by the weight and the geometric features of the plug. Plug 5 thereby acts as a means for protecting the chamber from overpressures.

In the example shown in the drawing, the upper and lower bodies of the device are screwed or threaded together.

Threading operations are facilitated through the use of knurlings 9 and 10.

The upper body comprises, at its upper end, an opening 11 for the passage of a tube 12 serving for the introduction of a bubbling gas. This tube is fastened to the upper body by a tightly threaded connection 13.

The lower body 3 comprises a port 14 where a draw-off pipe 15 is arranged. This pipe can be fastened by threads, the end of the pipe pressing onto joint 16.

The draw-off pipe can be connected to a value 17 in order to control the draining of cell 1. Value 17 and the draw-off pipe can be connected together through a tube joint 18 and a tube 19. The draining of cell 1 can be carried out by a peristaltic vacuum pump (not shown) located after value 17 and connected with the value through tube 20.

The lower body comprises, at its lower end, a housing 21 successively receiving, beginning from the bottom of the lower body, a joint 22, a filter-support grid 23 also serving as a crossbar, filtering means 24 and a joint 25. The lower edge 2a of the upper body 2 holds these parts in position on the bottom of the lower body 3 during the screwing together of bodies 2 and 3.

The support grid comprises passageways 26 allowing the bottom of the cell or second part of the cell and the central space 2b or first part of the cell to communicate.

Tube 12 is connected through a pipe 27 to a source of gas serving for the bubbling, such as a nitrogen cylinder under pressure 28. This pipe 27 comprises means for controlling the flow of bubbling gas 29.

The means for warming up cell 1 consist of a metallic heating unit 30 comprising heating resistors 31 controlled through electronic means 32 from a temperature-measuring sonde 33.

The lower and upper bodies 3 and 2 are made from fluorinated polymeric materials such as those marketed by the Du Pont de Nemours company under the brand TEFLON.

The filler joints 22 and 25 are made of VITON (which is a trademark of the Du Pont de Nemours company, possibly coated with TEFLON.

The support grid 23 is made of VOLTALEF, which is a trademark of the Atochem company.

The plug 5, as well as the connection 13, are made of TEFLON or VOLTALEF.

The different tubes, especially the bubbling gas inlet tube, are made of TEFLON.

The filtering means 24 may advantageously comprise two TEFLON filters having respectively filtering thresholds of 10 and 0.5 microns, the filter with a filtering threshold of 0.5 micron being placed above that with a filtering threshold of 10 microns. Such filters can be a LCWP filter (10 microns) and a FHLP filter (0.5 micron), both marketed by the MILLIPORE company.

Reference d represents the height which separates inlet port 34 in the bubbling gas cell from the upper face of filtering means 24.

In the embodiment of the drawings, of course, port 34 corresponds to the end of tube 12. Reference D1 represents the diameter of the cell at the level of the filtering means 24 and D2 is the diameter of the cell in its upper part.

The average diameter D of the cell may be defined as $(D1.V1+D2.V2)/(V1+V2)$ where V1 corresponds to the volume of the part of the cell with a diameter D1 and V2 to that with a diameter D2.

When the cell is not cylindric, diameter D represents the average equivalent hydraulic diameter of the useful part of the cell.

It is possible to obtain good results according to the present invention when the d/D ratio ranges from 0.15 to 0.25 and preferably from 0.17 to 0.21.

The flow of bubbling gas advantageously ranges from 0.2 to 0.3 times the volume of liquid contained in the cell per minute.

Tests have been successfully carried out by means of a substantially cylindric cell with a working volume of 200 cm$^3$ and a ratio liquid height to diameter close to 1.3, the distance d ranging from 8 to 10 mm and the flows of bubbling gas from 40 to 60 cm$^3$/minute.

An example of an operating procedure of the device is as follows.

The kerogens and the stable residues are prepared by removal of the carbonates with hydrochloric acid (HCL6N), followed by the removal of the silicates by a mixture of hydrofluoric acid (40% HF) and of HCL6N in a ⅜-⅛ proportion. The 40% HF is supplied by the Merck company, and the HCL6N is prepared from fuming HCL (Merck) with demineralized or distilled water.

The temperature of the attack acid solutions should never be lower than 70° C. within the device, in order to totally remove all the carbonates and silicates.

It is essential to carry out careful washings between the destruction of the carbonates and that of the silicates, in order to remove all the metal cations that might lead to the neoforming of fluorides and/or of fluorosilicates (in fact, these minerals contain OH groups which interfere with the organic elements, among others in elemental analysis). These washings are carried out with warm demineralized or distilled water (50° to 60° C.) which is filtered.

The maximum amount of rock which can be introduced into the device that has been previously described and dimensioned is 10 g. The rock is first crushed by means of a disk ring-roll crusher, or mortar, according to its hardness, then decarbonated. This decarbonation is carried out when cold in a beaker, with HCL6N and by stirring to decrease the effervescence, in order to avoid any material loss through overflow.

The device is placed on a support. The decarbonated rock is quantitatively transferred into the device by means of a funnel. It is filled with HCL6N. The device is put into the heating means and the temperature regulator is started up. Displaying 85° C. allows to obtain a temperature of 71° C. within the device. The HCL6N attack is let go on for 4 hours at least. Then, the device is emptied by starting up the peristaltic pump and by opening the communication cock, then it is again filled with HCL6N and the acid attack is let go on for about 12 hours.

At the end of this time, the device is emptied by filtering, then it is filled with warm demineralized or distilled water. Four washings are carried out. It is then filled with a mixture of HCL6N and 40% HF in a ⅛: ⅜ proportion. The plug is set back on the jacket. The acid attack is let take place for at least 8 hours or, better, for at least 12 hours.

This attack being finished, the acid is filtered. A washing with warm demineralized water is performed, and a new filling with HCL6N is achieved. The acid attack is let go on for 4 hours.

4 successive washings with warm demineralized water are achieved. The neutrality is checked with pH paper, then the device is dismantled to recover the kerogen.

The recovery takes place on the filter. The organic residue can be placed into a chiller and dried at 100° C. in a nitrogen stream, in a heating drier. If a microscopic survey is wished (optical analysis), it is recommended to avoid desiccation. It is possible to take an aliquot of the non-dried residue and to put it into a bottle with demineralized water and possibly a disperser.

The device according to the invention may also have other uses. It can generally be utilized for any treatment of a crushed rock and more particularly for preparations of the palynologic type (i.e. relating to organic residues of vegetables, such as spores and pollens) and for the extracting of organic matter through solvents.

We claim:

1. A laboratory device adapted to subject a same rock sample to successive treatments without any intermediary handling, comprising, in combination, a chamber having a first part and a second part, said first and second parts being secured together, said first part being fitted with means for introducing a rock sample and liquid reagents into the chamber, means for regulating the temperature of the chamber and means for protecting the chamber from an inner overpressure, said first part of the chamber further comprising means for stirring liquid within the chamber, said stirring means comprising a bubbling gas inlet adapted to introduce gas bubbles into liquid contained in said chamber, the second part of the chamber being located under said first part, selective filtering means interposed between said first and second parts of the chamber and having a porosity selected for retaining organic matter contained in the rock sample and freed by the liquid reagents, means hermetically joining said first part of the chamber, said filtering means and said second part of the chamber, means for draining off liquid passing across said filtering means and collecting in said second part of the chamber and means for controlling the draining off of liquid from said chamber; said means for protecting said chamber from an inner overpressure being adapted to liberate gas forming the bubbles from the chamber.

2. A device as claimed in claim 1, wherein said bubbling gas inlet is connected to a source of nitrogen.

3. A device as claimed in claim 1, wherein a d/D ratio of the device ranges from 0.15 to 0.25, d being a distance between the filtering means and a location in the chamber where said gas inlet discharges gas and D being the average hydraulic diameter of the chamber.

4. A device as claimed in any one of claims 1 to 3, wherein said device further comprises means for controlling the flow of bubbling gas and said control means is adapted to provide a gas flow ranging from 0.2 to 0.3 times a volume of liquid contained in the chamber per minute.

5. A device as claimed in claim 1, wherein said temperature regulation means comprises an electronically controlled metallic heating unit.

6. A device as claimed in claim 1, wherein said means for liberating the gas forming bubbles in said liquid comprises an open port in said first part and a plug kept in position within said open port by gravity on a substantially horizontal surface of said first part.

7. A device as claimed in claim 6, wherein said means for introducing the rock sample and the liquid reagents into the chamber comprises said open port.

8. A device as claimed in claim 1, wherein a d/D ratio of the device ranges from 0.17 to 0.21, d being a distance between the filtering means a location in the chamber where said gas inlet discharges the gas, and D being the average hydraulic diameter of the chamber.

9. A method of separating organic material contained in a rock sample, which comprises introducing a rock sample, in particulate form, into a chamber via an open port; introducing a first liquid reagent into said chamber; closing the open port with a plug which rests on a surface of the chamber and which provides a passage for liberating gas from said chamber upon the occurrence of an overpressure in said chamber; introducing an inert gas into said chamber as bubbles within the liquid reagent to effect stirring of the liquid reagent and the particulate rock sample; removing liquid reagent and separated mineral materials via a drain located at the bottom of said chamber via a filtering means positioned above the bottom of said chamber; correcting organic matter on said filtering means, and successively opening said port by removing said plug and introducing additional liquid reagents into said chamber followed by closing the port with said plug and by successive stirring with gas bubbles to effect further separation of the organic material from said rock sample.

10. A method as claimed in claim 9, further comprising providing a flow of the bubbling inert gas ranging from 0.2 to 0.3 times a volume of liquid contained in said chamber per minute.

* * * * *